United States Patent [19]

Warnow et al.

[11] 4,227,523
[45] Oct. 14, 1980

[54] RESPIRATOR CONSTRUCTION

[75] Inventors: Detlef Warnow, Gross Grönau; Hans-Jörg Ziebrecht, Lübeck, both of Fed. Rep. of Germany

[73] Assignee: Drägerwerk Aktiengesellschaft, Fed. Rep. of Germany

[21] Appl. No.: 1,409

[22] Filed: Jan. 8, 1979

[30] Foreign Application Priority Data

Jan. 14, 1978 [DE] Fed. Rep. of Germany ....... 2801546

[51] Int. Cl.$^3$ ............................................. A61M 16/00
[52] U.S. Cl. ........................... 128/204.24; 128/205.24
[58] Field of Search .................... 128/145.5–145.8, 128/204.24; 137/826, 624.15

[56] References Cited

U.S. PATENT DOCUMENTS

| Re. 29,778 | 9/1978 | Stewart | 128/145.8 |
| 3,957,047 | 5/1976 | Freytag et al. | 128/145.8 |
| 3,981,301 | 9/1976 | Warnow et al. | 128/145.8 |
| 4,057,059 | 11/1977 | Reid, Jr. | 128/145.8 |

FOREIGN PATENT DOCUMENTS 1287564 8/1972 United Kingdom ................. 128/145.8

Primary Examiner—Henry J. Recla
Attorney, Agent, or Firm—McGlew and Tuttle

[57] ABSTRACT

A respirator, particularly for infants, for supplying respiratory gas to a patient selectively according to an intermittent positive pressure ventilation cycle, an positive end expiratory pressure cycle, a continuous positive airway pressure cycle, and an intermittent mandatory ventilation cycle comprising, a respiration gas supply line connectable to a patient for supplying a respiratory gas to the patient, an expiration valve for switching from an inspiration phase to an expiration phase and back also connectable to the patient, and a first logic element connected to the expiration valve for switching the expiration valve from an inspiration phase to an expiration phase and back again. A pressure control system is connected to the first logic element for supplying gas at selected pressures to the expiration valve for the inspiration and expiration cycles thereof. A time control system is connected to the first logic element and the pressure control system which provides a selected time duration for an inspiration phase and an expiration phase. A source of static control pressure is derived from the respiration gas supply line and the pressure and time control systems both comprise a plurality of logic elements, each connectable to the static control pressure for controlling the inspiration and expiration phase switching, the selected pressures and the selected time durations.

8 Claims, 2 Drawing Figures

RESPIRATOR CONSTRUCTION

FIELD AND BACKGROUND OF THE INVENTION

The present invention relates to respirators in general and, in particular, to a new and useful respirator construction, particularly adapted for use with infants for providing a plurality of respiration cycles including the intermittent positive pressure ventilation cycle (IPPV), the positive end expiratory pressure (PEEP), the continuous positive airway pressure (CPAP) and the intermittent mandatory ventilation (IMV).

In order to obtain optimum therapeutic results when using respirator devices, it is necessary to design such respirators so that they can be adapted to different methods or cycles of operation which are proper for several respective physiological requirements.

Vitally nourished premature and newborn babies require first intermittent positive pressure ventilation (IPPV), which are combined primarily with an positive end-expiratory pressure (PEEP). After a recovery phase of the thorax muscles and beginning normalization of the blood gas values, respiratory gas with the necessary oxygen concentration can be given in spontaneous respiration, if necessary, under a continuously positive airway pressure (CPAP).

After prolonged use of respiration apparatus, the systems of respiratory patients frequently become accustomed to this type of respiration and, accordingly, they cannot return to adequate natural breathing without the use of breathing apparatus. Accordingly, for purposes of withdrawal, the number of breathing cycles to which the patient is subjected must be reduced slowly until such time as he is capable of breathing spontaneously (IMV).

In a known respirator, respiratory gas is conducted in a line current through preparations, indicating and safety devices, as well as through a branch with an opening for the patient, and is then discharged into the atmosphere over a control valve. The delivery of the gas maintaining the respiration from the control valve is controlled by different pressures by means of a pneumatic control, connected to the control valve, so that corresponding selective inspiration and expiration states are provided in the opening leading to the patient.

The pneumatic control contains a variable pneumatic oscillator which repeatedly produces two pressure levels, varying with a time corresponding to the duration of the inspiration and expiration phase, as well as a bistable pneumatic logic element which is switched between its two stable states in response to the latter. In this way, the connected control chamber of the control valve is exposed alternately to two different gas pressures. By linking elements and logic elements, it is thus possible to obtain a plurality of operating methods or cycles, such as the IPPV, PEEP-CPAP and IMV respiration method. For the sake of brevity, these cycles or methods will be referred to by their respective initials as used hereinbefore.

A disadvantage of this prior art respirator, which works on a dynamic control principle, is high gas consumption. This is caused by a constant gas loss in the throttles through which the amount of gas taken from the gas supply as control gas flows into the atmosphere after it has performed its switching functions. A known apparatus according to this principle has a gas consumption of about 4 liters per minute, while normally 0.5 to 3 liters per minute of respiratory gases are required for patients treated with this apparatus. (See German Patent Disclosure DOS No. 2,525,359).

SUMMARY OF THE INVENTION

The object of the present invention is to provide a respirator, particularly for infants, which is of a simple design, which uses pneumatic parts for the known types of respiration with a low gas consumption, and which permits mobile application.

The advantages achieved with this solution consist particularly in that proven static pneumatic elements are used for the entire control of the apparatus. The elements working on the static control principle consume hardly any respiratory gas and the control processes take place in closed systems. The amount of gas required for venting the small chambers and volumes is negligible.

Accordingly, an object of the present invention is to provide a respirator, particularly for infants, for supplying respiratory gas to a patient selectively according to IPPV, PEEP, CPAP and IMV cycles, comprising, a respiration gas supply line connectable to a patient for supplying a respiratory gas, an expiration valve for switching from an inspiration phase to an expiration phase and back, a first logic element connected to said expiration valve for switching said expiration valve from an inspiration phase to an expiration phase and back, pressure control means connected to said first logic element for supplying gas at selected pressures for said inspiration and expiration phases to said expiration valve, time control means connected to said first logic element and to said pressure control means for providing a selected time duration of said inspiration phase and a selected time duration for said expiration phase, a static control pressure line associated with said pressure and time control means, said pressure and time control means comprising a plurality of logic elements, each connectable with said static control pressure line for controlling said inspiration and expiration phase shifting, said selected pressures, and said selected time durations.

A further object of the invention is to provide a respirator construction which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
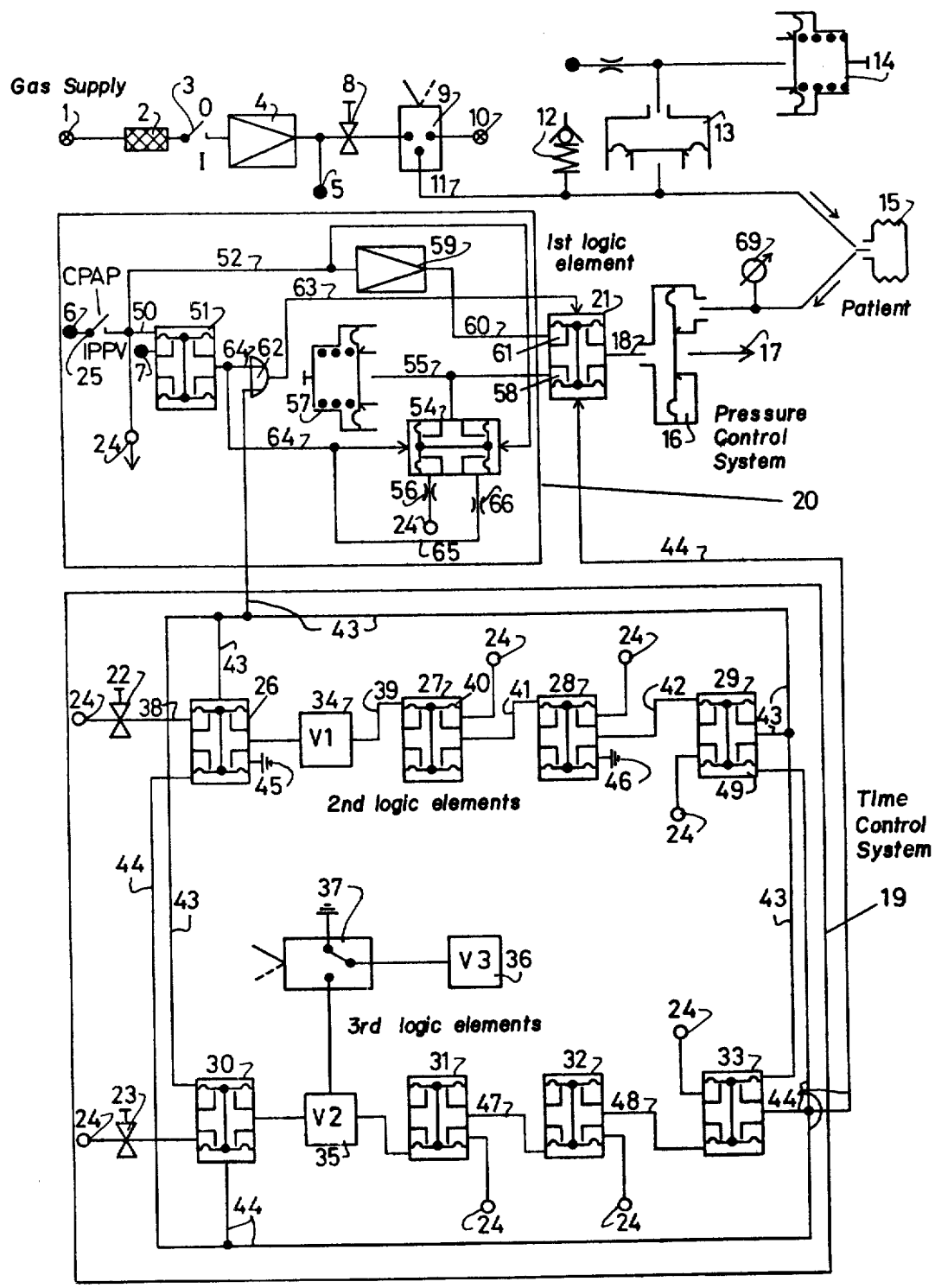
FIG. 1 is a schematic block diagram of the respirator, constructed in accordance with the present invention.

Respiratory gas is supplied under pressure to terminal 1 of the respirator and arrives over filter 2 at main switch 3. The following pressure reducer 4 adjusts the operating pressure or static control pressure which is supplied by terminal 5 to the supply terminals 6 and 7 which are shown spaced from the terminal 5 in FIG. 1, for clarity. A manually operated flow valve 8 regulates the respiratory gas flow, which is switched in mixer valve 9 to line 11. A mixer 10 can be connected during this switching. A supplementary air valve 12 and a pressure reducing valve 13 in line 11 are also provided in the direction of gas flow. Pressure reducer 13 is regulated by a valve 14 in known fashion.

The patient is represented symbolically by an elastic volume 15. The reversal of the inspiration and expiration phases is effected with an expiration valve 16. The patient breathes or exhales into the atmosphere through line 17. The control of expiration valve 16 is effected over line 18 through two control systems or means 19 and 20. The time control system 19 takes over the time control, and the pressure control system 20 controls the pressure. Both control systems transmit their signals to a first logic element 21. Each logic element used here can be understood to have two input terminals, one at 55 and one at 60 for element 21, one output terminal at 18 for element 21, and two control terminals 63 and 44 for element 21, any number of which can be used as needed.

The time control system 19 which effects the time control defines an inspiration time with a first regulating element 22, and an expiration time with a second regulating element 23. Both regulating elements 22 and 23 are pneumatically supplied from terminals 24, which are arranged downstream of a CPAP/IPPV selector switch 25. All terminals 24 are assumed to be connected in common in FIGS. 1 and 2. The time control system 19 is composed of pneumatic logic elements or second logic element means 26 to 29 with volume V1 at 34, pneumatic third logic element means 30 to 33 with volume V2 at 35, and a switch 37 with volume V3 at 36. The first regulating element 22 which is set for finely dosing, is supplied over terminal 24 with gas under pressure. The pressure gas flows over line 38 through the second logic element 26 to Volume V1 at 34, then over line 39 to chamber 40 of the second logic element 27. The constant pressure control from 24 to the second logic element 27 yields a 1-value signal in line 41 and, correspondingly, a 0-value signal in line 42.

A 1-value signal is equal to an operating pressure with a 0-value signal equalling a zero pressure. The exponential pressure rise in volume V1, 34, line 39 and chamber 40 leads, at 0.8 p (where p=operator pressure at terminal 5 and at terminal 24) to the switching of the second logic element 27, so that line 41 drops to a 0-signal and line 42 shows a 1-signal. This in turn switches the second logic element 29 so that terminal 24 is connected with line 43 and line 43 thus has a 1-value signal. Terminals 24 can be considered as part of the static control pressure line 5 which is connected downstream of CPAP/IPPV switch 25. The 1-value signal in line 43 now switches line 44, which is downstream of the third logic element 33, to a 0-signal. At the same time, the second logic element 26 blocks, so that volume V1, 34 is vented over de-aerator or vent 45.

Chamber 40 thus also becomes pressureless. Terminal 24 is again connected with line 41, the 1-value signal in line 41 blocks the second logic element 28 and line 42 can be de-aerated or vented over vent 46. The 0-value signal in line 42 does not influence the switching of the second logic element 29 due to pressure at 24. Element 29, together with the third logic element 33, thus form a bistable storage. The 1-value signal in line 43 likewise controls the third logic element 30, so that pressure gas can flow from terminal 24 over the finely dosing second logic element 23, the third logic element 30 to volume V2, 35 and to the third logic element 31. The exponential pressure rise in volume V2, 35 leads likewise to switching of the third logic element 31 at a pressure of 0.8p. Line 47 receives a 0-value signal, and thus lines 48 and 44 experience a 1-value signal. Line 44 reverses the second logic element 29 over pressure p in chamber 49, so that line 43 now receives a 0-value signal. The third logic element 33 is thus bistable again on line 44 as part of the storage consisting of the second logic element 29 and the third logic element 33.

Line 44 blocks the third logic element 30 and opens the second logic element 26, and then the cycle starts again. The charging time of the volumes V1, 34 and V2, 35 which can be set by hand at the first regulating element 22 and the second regulating element 23, thus determines the clock time of the 1-value signal in line 43 and in line 44, respectively.

The functional group carrying out the IMV cycle (spontaneous breathing) is contained in the time control system 19. The technical requirement for carrying out the IMV cycle or method consists in the extension of the expiration time, which can be exactly fixed in time while maintaining the inspiration time. This requirement is met with reversing switch 37 by adding volume V3, 36 to volume V2, 35. The charging time thus obtained yields an (n+1)-fold expiration time corresponding to the n-fold size of colume V3, 36. Filling volumes V1, V2 and V3 can generally be defined as first, second and third volume means, respectively. That is, the expiration time is increased as a function of the size of V3.

The pressure control system 20 for carrying out the pressure control is supplied with pressure gas over terminal 6, when the CPAP/IPPV selector switch 25 is brought into the IPPV position which is closed for an intermittent positive pressure respiration cycle. Operating pressure for the time control system 19 is then applied to terminal 24. A fourth logic element 51 is triggered over a line 50 and is thus blocked with respect to operating pressure at terminal 7. A fifth logic element 54 thus receives a 0-value signal from line 64 so that the passage from terminal 24 to line 55 is opened. Terminal 24 is here conducted through a second throttle 56 to be adapted in order to limit the gas flow. The pressure in line 55 can be regulated by hand by pressure regulating valve 57. Line 55 leads into chamber 58 of the first logic element 21. A pressure reducer 59 is also supplied over a line 52 which works with a constant back pressure of about 0.15 bar. The pressure gas is conducted at this pressure over line 60 into chamber 61 of the first logic element 21.

If a 1-value signal appears in line 44 of the time control system 19, line 44 controls the first logic element 21 so that line 60 is connected with a line 18. The back pressure of pressure reducer 59 thus acts on expiration valve 16, which is closed, thus blocking the expiration path of the patient through line 17 into the atmosphere. The patient is treated with the respiratory gas fed through line 11. With the appearance of the 1-value signal in line 44, the 0-value signal in line 43 becomes the 1-value signal after a time. This 1-value signal in line 43 then arrives over OR-element 62 in line 63 and triggers the first logic element 21, so that the passage from chamber 61 to line 18 is blocked. The passage from line 55 over chamber 58 in line 18 is open. Pressure regulating or back pressure regulating valve 57 in line 55 permits adjustment of the pressure between zero to about 20 mbar, which then acts over line 18 on expiration valve 16. With a pressure of 0 bar, the patient can expire freely into the atmosphere. With any other setting, the patient expires with this desired end expiration pressure (PEEP). The pressure can be checked on manometer 69.

If the CPAP-method or cycle is to be used for constant positive pressure breathing instead of the IMV-method, the CPAP/IPPV selector switch 25 must be brought into position CPAP, hence opened. The pressure gas supply from terminal 6 to line 50 is thus interrupted, and the entire pressure system 19 is left pressureless. This results in a 0-value signal for the two lines 43, 44. In the fourth logic element 51, terminal 7 is connected over line 64 with OR element 62. The gas pressure thus also acts on line 63 and controls the first logic element 21 in such a way that line 55 is connected over chamber 58 with line 18. At the same time, line 65 is supplied over line 64, and the fifth logic element 54 is controlled so that line 65 is connected over a first throttle 66 with line 55. The gas pressure regulated with pressure regulating valve 57 in line 55 acts over line 18 on expiration valve 16. The patient expires against this adjustment low overpressure.

A mixer 10 working with low pressure on its outlet in an extension of the respirator can be connected over a mixer valve 9 to the supply of the patient.

Figure 2:
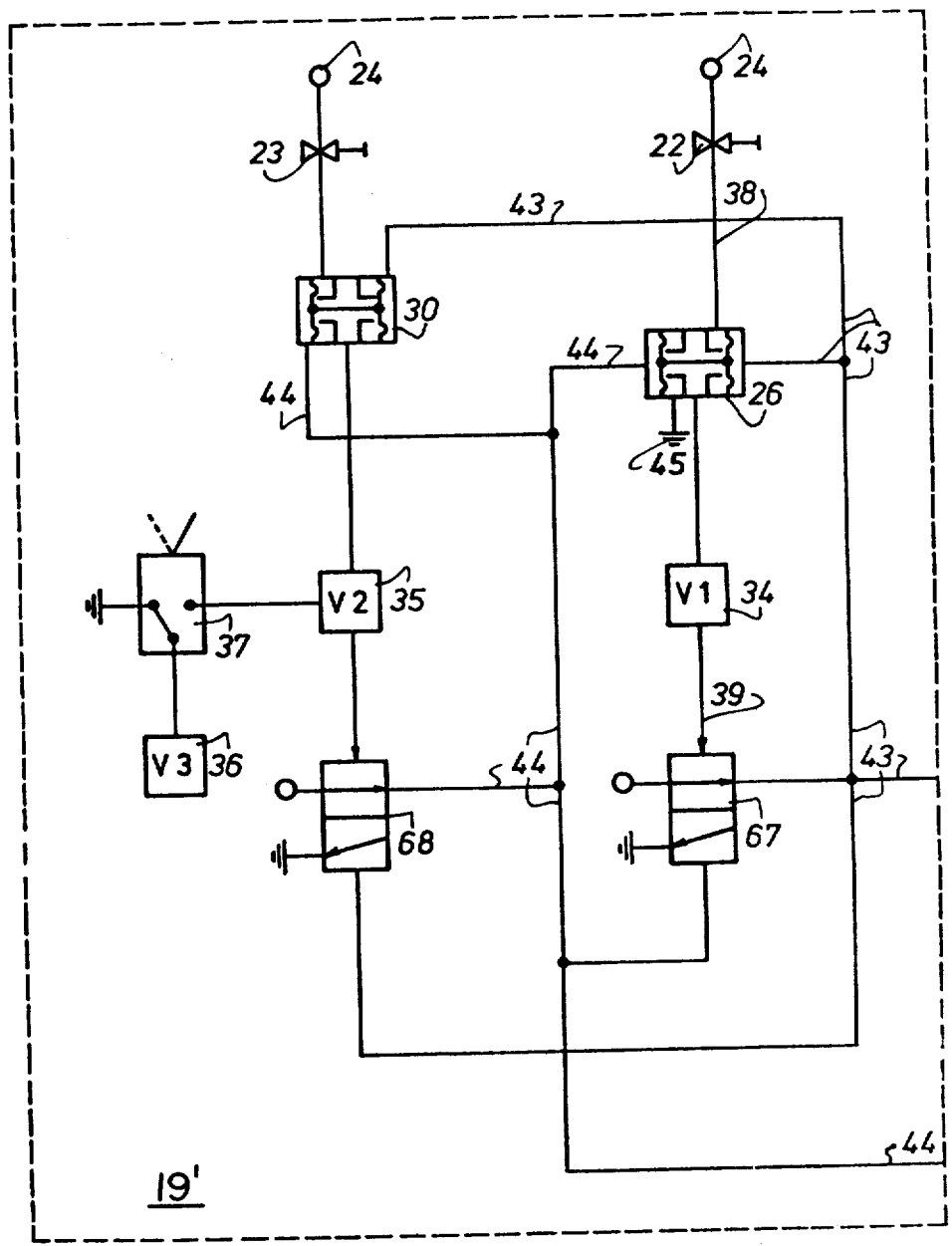
FIG. 2 is a schematic block diagram of one additional embodiment for the time duration system 19 utilized in the schematic circuit of FIG. 1.

In another embodiment of the invention, the time control system 19 can be replaced by system 19', as shown in FIG. 2, with pneumatic functional elements, for example, piston elements. The feature of transforming the pressure switching value in the pneumatic capacities over a double negation into a 1-value signal for the second logic element 29 and the third logic element 33, which is necessary with the second logic element means 27, 28, 29 and the third logic element means 31, 32 and 33 for switching reasons, is eliminated here.

System 19' is used in place of system 19 in FIG. 1, with the pressure control system 20 of FIG. 1. For this embodiment of the invention, lines 43 and 44 of system 19' are connected to lines 43 and 44 of system 20 with terminals 24 of 19' common to those of system 20.

The switching characteristic of the first functional element or means 67 and of the second functional element or means 68 requires that a certain switching pressure must first have been attained in order to obtain a sudden reversal. The cycle then takes place in the same manner as described above for the time control system 19 of FIG. 1 in connection with the functioning of system 20. Means 67 and 68 are shown here as values but may be other logic element means.

While specific embodiments of the invention have been shown and described in detail to illustrate the applicatin of the principles of the invention, it will be understood that the invention may be embodied otherwise without departing from such principles.

What is claimed is:

1. A respirator, particularly for infants, for supplying respiratory gas to a patient selectively according to IPPV, PEEP, CPAP and IMV cycles, comprising:

(a) a respiration gas supply line connectable to a patient for supplying a respiratory gas;
    (b) an expiration valve for switching from an inspiration phase to an expiration phase and back connected to said respiration gas supply line;
    (c) a first logic element connected to said expiration valve for switching said expiration valve from an inspiration phase to an expiration phase and back;
    (d) pressure control means connected to said first logic element for supplying gas at selected pressures to said first logic element for controlling said inspiration and expiration phases of said expiration valve for IPPV, CPAP and PEEP cycling;
    (e) time control means connected to said first logic element and said pressure control means for providing a selected time duration for said inspiration phase and a selected time duration for said expiration phase; and
    (f) a static control pressure line associated with said pressure and time control means; said time control means comprising a first regulating element connected to said static control pressure line, second logic element means connected to said first regulating element, said first regulating element and said second logic element means provided for controlling said selected time duration for said inspiration phase, a first volume in said second logic element means fillable by gas pressure from said static control pressure line to define said selected time duration for said inspiration phase, a second regulating element connected to said static control pressure line, third logic element means connected to said second regulating element, said second regulating element and third logic element means controlling said selected time duration for said expiration phase, a second volume in said third logic element means fillable by gas pressure from said static control pressure line for defining said selected time duration of said expiration phase, a third volume connected to said second volume means, and a reversing switch connected between said second and third volumes, said third volume being fillable by gas from said second volume via said reversing switch to selectively add an additional time duration to said expiration phase whereby the respirator functions according to IMV cycles.

2. A respirator, as claimed in claim 1, wherein said second logic element is connected in series with said first regulating element, said first volume being series connected with a portion of said second logic element, and said second logic element includes a pneumatic first functional element series connected with said first volume, said pneumatic first functional element connected to said pressure control means, said third logic element connected to said second regulating element in series, said second volume series connected to a portion of said third logic element, said third logic element further including a pneumatic second functional element series connected to said second volume, said pneumatic second functional element connected to said first logic element.

3. A respirator, as claimed in claim 1, wherein said pressure control means includes an OR-element having two inputs and one output, one of said inputs connected to said time control means, said pressure control means further including a fourth logic element connected between said static control pressure line and the other of said inputs of said OR-element, a CPAP/IPPV selector switch connected between said static control pressure line and said fourth logic element, said time control means connected to said static control pressure line downstream of said CPAP/IPPV selector switch, a fifth logic element connected to said fourth logic element at a control terminal of said fifth logic element and at an input terminal of said fifth logic element, a first throttle connected between said input terminal of said fifth logic element and said fourth logic element, said fifth logic element having a second input terminal connected to said static control pressure line downstream of said CPAP/IPPV selector switch, a second throttle connected between said static control pressure line and said second input terminal of said fifth logic element, said fifth logic element having an output connected to said first logic element, and a pressure reducer for establishing a constant reduced pressure connected between said static control pressure line downstream of said CPAP/IPPV selector switch and said first logic element.

4. A respirator, as claimed in claim 1, wherein said pressure control means comprises a CPAP/IPPV selector switch connected to said static control pressure line, said static control pressure line including a control line portion extending downstream of said CPAP/IPPV selector switch, a fourth logic element having one control terminal connected to said control line portion and one input terminal connected to said static control pressure line, an OR-element connected to an output terminal of said fourth logic element, said OR-element having two input terminals and an output terminal, said output terminal of said OR-element connected to one control terminal of said first logic element, a pressure reducer for reducing the pressure of gas in said static control pressure line connected between said control line portion and an input terminal of said first logic element, a fifth logic element having one control terminal connected to said output terminal of said fourth logic element, an input terminal of said fifth logic element connected to said output terminal of said fourth logic element, a first throttle between said output terminal and said fourth logic element and said input terminal of said fifth logic element, said control line portion connected to another input terminal of said fifth logic element, a second throttle connected between said control line portion and said other input terminal of said fifth logic element, said fifth logic element including an output terminal connected to another input terminal of said first logic element, a back pressure regulating valve connected to said other input terminal of said first logic element, an output terminal of said first logic element connected to said expiration valve for applying a back gas pressure to said expiration valve for initiating said inspiration phase and for applying a back pressure to said expiration valve during said expiration phase, said time control means connected to the other input of said OR-element.

5. A respirator, as claimed in claim 4, wherein said time control means further comprises first and second regulating elements connected to said control line portion for supplying a reduced gas flow from that of said control line portion, said CPAP/IPPV selector switch being opened to place the respirator in a CPAP cycle and reduced pressure in said control line portion to zero for stopping the operation of said time control means, and said CPAP/IPPV selector switch being closed to apply a static control pressure to said control line portion from said static control pressure line for placing the respirator in a IPPV cycle and allowing the operation of said time control means, a logic element (26) having an input terminal connected to said first regulating element, a first volume connected to an output terminal of said logic element (26) for containing an exponentially increasing pressure from said control line portion which defines said duration of said inspiration phase, a logic element (27) having one control terminal connected to said first volume and an input terminal connected to said control line portion, a logic element (28) having a control terminal connected to an output terminal of said logic element (27) and an input terminal connected to said control line portion, a logic element (29) having a control terminal connected to an output terminal of said logic element (28) and an input terminal connected to said control line portion, an expiration control line (43) connected to a control terminal of said logic element (26) and an output terminal of said logic element (29), said expiration control line connected to said other terminal of said OR-element of said pressure control means, a logic element (30) having an input terminal connected to said second regulating element and one control terminal connected to said expiration control line, a second volume connected to an output of said logic element (30) for containing an exponentially increasing pressure from said control line portion which defines said time duration of said expiration phase, a logic element (31) having one control terminal connected to said second volume and an input terminal connected to said control line portion, a logic element (32) having a control terminal connected to an output terminal of said logic element (31) and an input terminal connected to said control line portion, a logic element (33) having a control terminal connected to an output terminal of said logic element (32) and having an input terminal connected to said control line portion, another control terminal of said logic element (33) connected to said expiration control line, an inspiration control line connected to an output of said logic element (33) and connected to another control terminal (49) of element (29), said inspiration control line connected to another control terminal of said first logic element, another control terminal of said logic element (30) and another control terminal of logic element (26).

6. A respirator, as claimed in claim 5, including a selector switch connected to said second volume, and a third volume connected to said selector switch for receiving gas from said control line portion and containing an exponentially increasing pressure which defies an additional duration time applied to said second volume for adding said additional duration time to said expiration phase.

7. A respirator, as claimed in claim 6, including vents connected to another input terminal of said logic elements (26), (28), (30) and (32).

8. A respirator, particularly for infants, for supplying respiratory gas to a patient selectively according to the IPPV, PEEP, CPAP AND IMV cycles, comprising:
 (a) a respiration gas supply line connectable to a patient for supplying a respiratory gas;
 (b) expiration valve means for switching from an inspiration phase to an expiration phase and back connected to said respiration gas supply line;
 (c) a first logic element for switching said expiration valve means from an inspiration phase to an expiration phase and back, said first logic element having first and second control inputs, first and second supply inputs, and one output connected to said expiration valve means for switching said expiration valve means;
 (d) pressure control means connected to said first control input and said first and second supply inputs of said first logic element for supplying gas at selected pressures to said first and second supply inputs and said first control input, for controlling said inspiration and expiration phases of said expiration valve means for IPPB, CPAP and PEEP cycles;

(e) time control means connected to said second control input of said logic element and to said pressure control means for providing a selected time duration for said inspiration and expiration phase and for providing an IMV cycle; and (f) a static control pressure line connected to said pressure and said time control means for supplying a static control pressure thereto for supplying gas at said selected pressures and for said selected time durations.

* * * * *